United States Patent [19]
Bowden et al.

[11] Patent Number: 5,907,070
[45] Date of Patent: *May 25, 1999

[54] PREPARATION OF HALOGENATED ALCOHOLS

[75] Inventors: Martin Charles Bowden, Brighouse; Stephen Martin Brown, Cumberworth; Trevor Robert Perrior, Wokingham, all of United Kingdom

[73] Assignee: Zeneca Limited, London, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/765,532

[22] PCT Filed: Nov. 2, 1995

[86] PCT No.: PCT/GB95/02571

§ 371 Date: Jan. 6, 1997

§ 102(e) Date: Jan. 6, 1997

[87] PCT Pub. No.: WO96/16010

PCT Pub. Date: May 30, 1996

[30] Foreign Application Priority Data

Nov. 24, 1994 [GB] United Kingdom .................. 9423746

[51] Int. Cl.$^6$ ....................................................... C07C 33/42
[52] U.S. Cl. ........................................... 568/845; 568/843
[58] Field of Search .................................. 568/849, 841, 568/842, 843, 448, 845

[56] References Cited

PUBLICATIONS

Merz and Tomahogh, Chem. Ber, 110, 96–106 (1977), "Reactions of Aldehydes and Ketones with the Makosza Dichlorocarbene Reagent".

Kaspar and Wiechert, Chemische Berichte Jahrg, 91, 2664–2670 (1958), "Uber die Einwirkung von Haloform auf Steroidcarbonylfunktionen".

Shono et al., Additttion of Trichloromethyl Anion to Aldehydes or Vinyl Acetate, Tetrahedron Lett. 1981, 22(9), 871–4, 1981.

Shono et al., Chain Reactions Induced by Cathodic Reactions, J. Org. Chem., 50, 2527–2533, 1985.

*Primary Examiner*—Samuel Barts

[57] ABSTRACT

The invention provides an improved process for preparing halogenated alcohols of the formula $CX_1X_2X_3CH(OH)CH:C(CH_3)_2$ (I, $X_1$, $X_2$, $X_3$=halo) by reacting $CX_1X_2X_3H$ with 3-methylbut-2-en-1-al in the presence of a strong base and an inert solvent.

9 Claims, No Drawings

PREPARATION OF HALOGENATED ALCOHOLS

This a 371 application of PCT/GB95/02571 filed Nov. 2, 1995.

This invention relates to halogenated alcohols and more particularly to a process of preparing halogenated alcohols from haloalkanes.

The preparation of halogenated alcohols such as 1,1,1-trichloro-4-methyl-3-penten-2-ol has previously been described (in for example J. Chem.Soc. (C), 1976,670). In this process a Grignard reagent such as isobutenylmagnesium chloride is reacted with chloral. However the Grignard reaction is essentially a laboratory procedure and is not inherently suitable for industrial production. An alternative known process involves the reaction of chloral with isobutylene under the conditions of the Prins reaction but this can lead to a mixture of the desired product with the isomeric 1,1,1-trichloro-4-methyl-4-pentene-2-ol and further treatment to isomerise this is required.

The present invention is concerned with an improved process which is applicable to the preparation of the desired compounds and which is suitable for industrial manufacture.

Accordingly the present invention provides a process for preparing a halogenated alcohol of formula:

$$CX^1X^2X^3\text{—}CH(OH)CH\text{=}C(CH_3)_2 \quad (I)$$

wherein $X^1$, $X^2$ and $X^3$ are halo, preferably chloro, bromo or fluoro, although not all of $X^1$, $X^2$ and $X^3$ are necessarily the same, which comprises reacting a compound of formula:

$$CX^1X^2X^3H \quad (II)$$

with 3-methylbut-2-en-1-al in the presence of a strong base and a solvent.

Compounds of formula (I) which may be made by the process include those wherein $X^1$, $X^2$ and $X^3$ are all chloro or all bromo. Particular examples of such compounds of formula (I) include 4-hydroxy-2-methyl-5,5,5-tribromopent-2-ene, and 4-hydroxy-2-methyl-5,5,5-trichloropent-2-ene.

The compounds of formula (II) which are useful in the process of the invention are halomethanes containing a single hydrogen atom, such as chloroform, and bromoform. 3-Methylbut-2-en-1-al is also known as senecialdehyde.

The process is conducted in the presence of a strong base, which is believed to act by generating a perhaloalkyl ion which then reacts with the aldehyde. Suitable strong bases include alkali metal lower alkoxides, such as sodium or potassium alkoxides containing up to 6 carbon atoms, for example sodium isopropoxide, potasium isopropoxide, sodium t-butoxide and potassium t-butoxide, but other bases such as alkali metal hydrides, for example sodium hydride, and amides, for example sodamide, may also be used.

The process is preferably conducted at low temperatures to avoid the production of unwanted by-products. A preferred temperature is within the range −80° C. to 0° C., especially where a polar aprotic solvent is used. Particular examples of polar aprotic solvents which may be useful in the process include amides such as dimethylformamide, dimethylacetamide, dibutylacetamide, cyclic ethers such as tetrahydrofuran, tetrahydropyran and dioxan, glycol ethers such as ethylene glycol dimethyl ether, and ethylene glycol diethyl ether, and sulphoxides such as dimethyl sulphoxide. However other inert solvents such as aromatic hydrocarbons e.g. toluene may also be used.

The process is useful to produce the compounds of formula (I) in good yield and purity and allows for easy isolation of the desired product. Any unreacted or excess compound of formula (II) can be readily recovered and recycled.

The compounds of formula (I) are useful as intermediates in a variety of synthetic procedures for the manufacture of useful products. Thus 4-hydroxy-2-methyl-5,5,5-trichloropent-2-ene may be used in the manufacture of permethrin acid, a key intermediate for pyrethroid insecticides, by the process set out in UK Patent No. 1528944.

The process of the invention is illustrated by the following Examples.

EXAMPLE 1

This Example illustrates the preparation of 4-hydroxy-methyl-5,5,5-tribromopent-2-ene.

Sodium t-butoxide (1.2 ml of a 42% solution in dry dimethylformamide) was added dropwise over a period of 20 minutes to a stirred mixture of bromoform (1.14 g), 3-methylbut-2-ene-1-al (0.32 g) and dry tetrahydrofuran (15 ml) maintained at a temperature of −65° C. by external cooling under a nitrogen atmosphere, and the stirred mixture maintained at that temperature for a further 30 minutes after completion of the addition. The external cooling was removed and the reaction quenched by dropwise addition of a saturated aqueous ammonium chloride solution until the temperature had risen to −20° C. The mixture was thereafter stirred until the temperature had risen to ambient (ca.20° C.).

The aqueous and organic phases were separated and the aqueous phase extracted with dichloromethane (2×20 ml) and the extracts combined with the organic phase and dried over anhydrous sodium sulphate. After removal of the solvents by evaporation under reduced pressure the residue was dissolved in hexane (20 ml) and the solution washed with brine (3×5 ml) and dried over anhydrous sodium sulphate, and concentrated by removal of the solvent under reduced pressure. The residue was dissolved in a mixture of ethyl acetate and petroleum ether (boiling range 40–60° C.) (1:6 parts by volume, 20 ml) and purified by loading onto a short silica column (3.75 cm) and eluting with the same mixture (400 ml). Successive fractions (3) were examined by chromatography to establish that the desired product was present in the first two fractions. The eluate was concentrated by evaporation of the solvents under reduced pressure and the residue (1.14 g) identified by nuclear magnetic resovance spectroscopy and gas chromatographic-mass spectral analysis as 4-hydroxy-2-methyl-5,5,5-tribromopent-2-ene.

EXAMPLE 2

This Example illustrates the preparation of 4-hydroxy-2-methyl-5,5,5-trichloropent-2-ene.

The procedure and quantities used were similar to those of Example 1 except that chloroform (0.54 g) was used in place of bromoform. The product was obtained as a white crystalline solid (0.594 g).

We claim:

1. A process for preparing a halogenated alcohol of formula:

$$CX^1X^2X^3\text{—}CH(OH)CH\text{=}C(CH_3)_2 \quad (I)$$

wherein $X^1$, $X^2$ and $X^3$ are halo, which comprises reacting a compound of formula:

$$CX^1X^2X^3H \quad (II)$$

with 3-methylbut-2-en-1-al in the presence of an alkali metal alkoxide, at a temperature within the range −80 to 0° C. and an inert polar aprotic solvent.

2. A process according to claim 1 wherein the alkali metal alkoxide is selected from sodium isopropoxide, potassium isopropoxide, sodium t-butoxide and potassium t-butoxide.

3. A process according to claim 1 wherein the solvent is tetrahydrofuran.

4. A process as claimed in claim 1 wherein the compound of formula (II) is selected from chloroform and bromoform.

5. A process as claim in claim 1 wherein the temperature is below −20° C.

6. A process for the preparation of 4-hydroxy-2-methyl-5,5,5-trichloropent-2-ene which comprises reacting chloroform with 3-methylbut-2-en-1-al in the presence of an alkali metal alkoxide, at a temperature within the range −80 to 0° C. and a polar aprotic solvent.

7. A process as claimed in claim 6 wherein the alkali metal alkoxide is sodium or potassium t-butoxide.

8. A process according to claim 6 wherein the temperature is below −20° C.

9. A process according to claim 6 wherein the polar aprotic solvent is tetrahydrofuran.

* * * * *